US009861469B2

(12) United States Patent
Simonov et al.

(10) Patent No.: US 9,861,469 B2
(45) Date of Patent: *Jan. 9, 2018

(54) ACCOMMODATING INTRAOCULAR LENS WITH HAPTICS FOR SULCUS FIXATION

(71) Applicant: Akkolens International B.V., Breda (NL)

(72) Inventors: Aleksey Nikolaevich Simonov, The Hague (NL); Michiel Christiaan Rombach, Breda (NL)

(73) Assignee: Akkolens International B.V., Breda (NL)

( * ) Notice: Subject to any disclaimer, the term of this patent is extended or adjusted under 35 U.S.C. 154(b) by 1 day.

This patent is subject to a terminal disclaimer.

(21) Appl. No.: 14/271,578

(22) Filed: May 7, 2014

(65) Prior Publication Data
US 2014/0336757 A1 Nov. 13, 2014

(30) Foreign Application Priority Data
May 7, 2013 (NL) .................................... 2010769

(51) Int. Cl.
A61F 2/16 (2006.01)
(52) U.S. Cl.
CPC .......... *A61F 2/1629* (2013.01); *A61F 2/1632* (2013.01); *A61F 2/1648* (2013.01); *A61F 2/1651* (2015.04); *A61F 2002/1681* (2013.01); *A61F 2002/1682* (2015.04); *A61F 2002/1683* (2013.01); *A61F 2002/1689* (2013.01); *A61F 2220/0008* (2013.01)
(58) Field of Classification Search
CPC ....................... A61F 2/1632; A61F 2002/1682

USPC ....................................................... 623/6.34
See application file for complete search history.

(56) References Cited

U.S. PATENT DOCUMENTS

| 5,766,244 A | 6/1998 | Binder |
| 8,603,167 B2 | 12/2013 | Rombach |
| 2003/0199977 A1 | 10/2003 | Cumming |
| 2006/0238702 A1 | 10/2006 | Glick et al. |
| 2008/0046076 A1 | 2/2008 | Rombach |
| 2008/0215146 A1 | 9/2008 | Rombach |
| 2009/0062912 A1 | 3/2009 | Rombach |
| 2010/0094413 A1 | 4/2010 | Rombach et al. |
| 2010/0106245 A1 | 4/2010 | Rombach et al. |

(Continued)

FOREIGN PATENT DOCUMENTS

| CN | 101137339 A | 3/2008 |
| HK | 1101669 A1 | 5/2010 |

(Continued)

*Primary Examiner* — David H Willse
*Assistant Examiner* — Javier Blanco
(74) *Attorney, Agent, or Firm* — The Webb Law Firm

(57) ABSTRACT

An accommodating intraocular lens construction includes a lens of fixed optical power to correct refractive error and a lens of variable power to restore accommodation of the eye, which variable lens can have two optical elements which either shift perpendicular to the optical axis, or which variable lens can have two elements which move along the optical axis. The accommodating intraocular lens has at least one haptic to provide transfer of movement to at least one of the optical elements and at least one additional haptic for sulcus fixation to provide limitation of movement of at least one component of the lens along the optical axis. The movement of the additional haptic is largely independent from the haptic for movement.

4 Claims, 3 Drawing Sheets

(56) References Cited

U.S. PATENT DOCUMENTS

| | | | |
|---|---|---|---|
| 2010/0131061 A1 | 5/2010 | Callahan et al. |
| 2010/0280609 A1 | 11/2010 | Simonov et al. |
| 2011/0144746 A1 | 6/2011 | Vanderbilt |
| 2012/0257278 A1 | 10/2012 | Simonov et al. |
| 2012/0310341 A1 | 12/2012 | Simonov et al. |
| 2012/0310342 A1 | 12/2012 | Nguyen et al. |
| 2012/0323320 A1 | 12/2012 | Simonov et al. |
| 2012/0323321 A1 | 12/2012 | Simonov et al. |

FOREIGN PATENT DOCUMENTS

| | | |
|---|---|---|
| JP | 2005161075 A | 6/2005 |
| JP | 2006034917 A | 2/2006 |
| MX | 2011005583 A | 10/2011 |
| WO | 2010131955 A1 | 11/2010 |
| WO | 2012105843 A1 | 8/2012 |
| WO | 2013055212 A1 | 4/2013 |

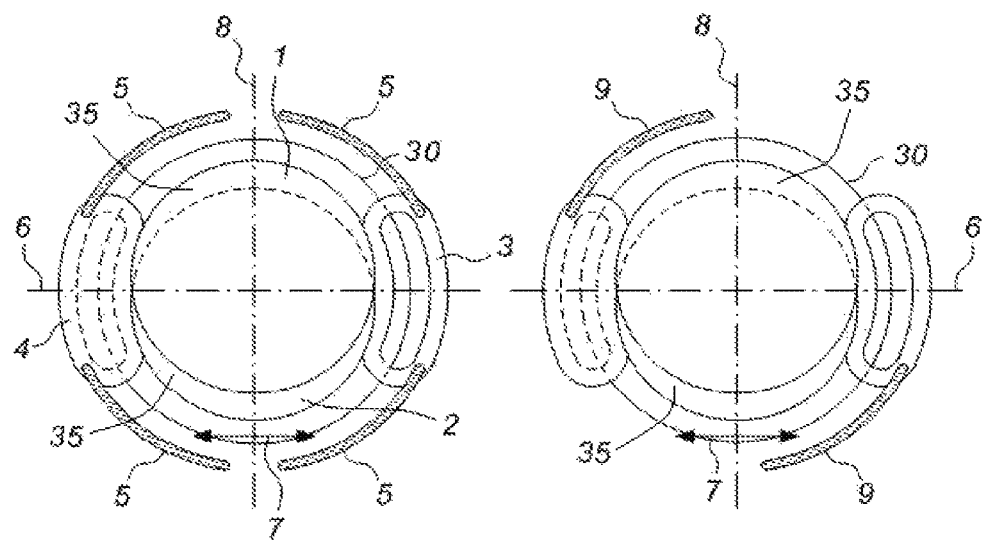
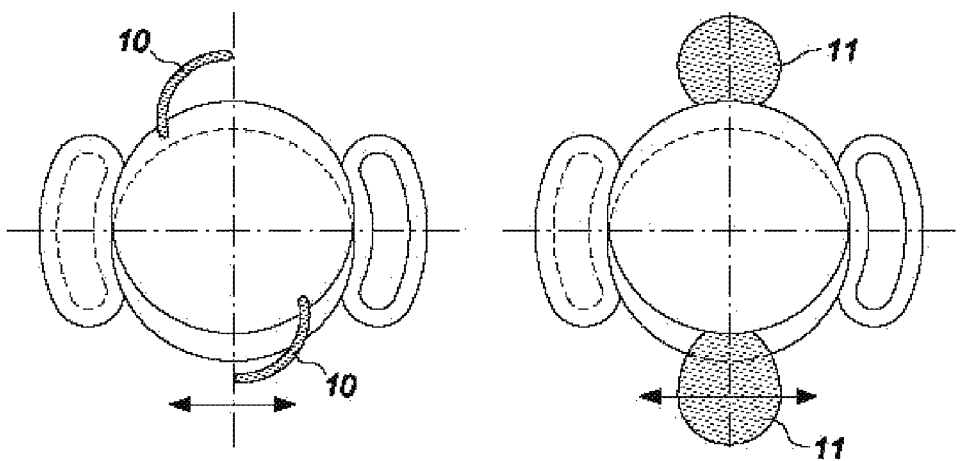
Fig. 1   Fig. 2   Fig. 3   Fig. 4

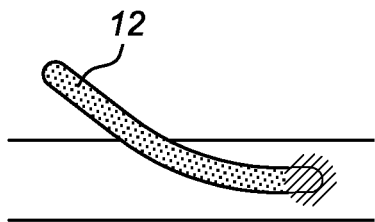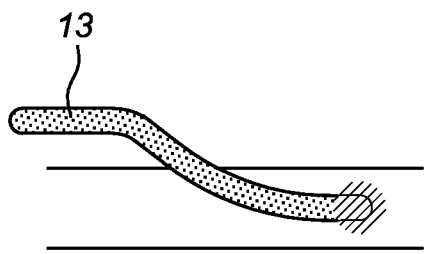
Fig. 5    Fig. 6
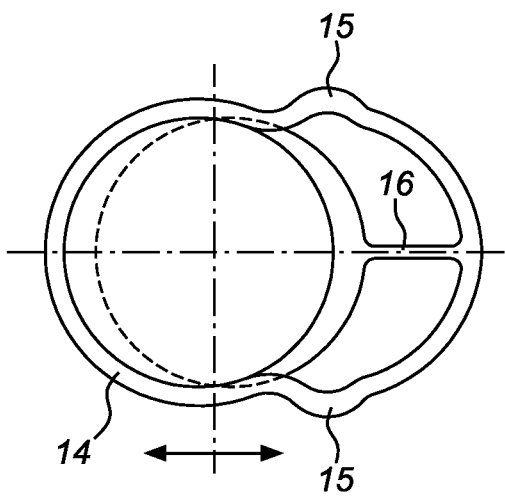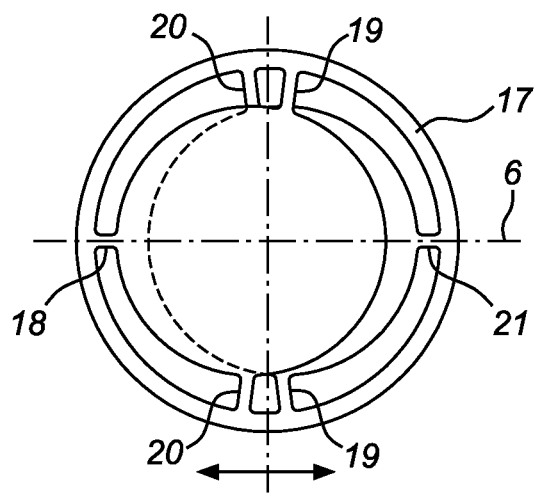
Fig. 7    Fig. 8

ACCOMMODATING INTRAOCULAR LENS WITH HAPTICS FOR SULCUS FIXATION

CROSS REFERENCE TO RELATED APPLICATION

This application claims priority to Netherlands Patent Application No. 2010769 filed May 7, 2013, the disclosure of which is hereby incorporated in its entirety by reference.

BACKGROUND OF THE INVENTION

The present document discloses haptics arrangements for sulcus fixation of an accommodating intraocular lens construction. The lens construction is adapted in such a way that, first, it provides fixation of the construction in the sulcus of the eye and, second, at least one component of the construction remains free to move in a direction perpendicular to the optical axis providing variable focus of a variable lens of which principles are set forth below.

SUMMARY OF THE INVENTION

The lens construction includes, for optical functions, at least one lens of fixed optical power to correct the refractive error of the aphakic eye, i.e. eye without a natural lens. The fixed-power lens comprises at least one optical surface, preferably spherical surface, adapted to correct refractive error of the eye. In addition, the fixed-power lens may comprise aspherical optical surfaces to correct other aberrations of the eye, for example, astigmatism. The degree of correction and type of the aberrations can be determined from a number of biometric measurements as well as optical modelling of the eye, e.g. using optical ray-tracing software.

The lens construction, or for brevity, construction also includes at least one lens of variable optical power to restore accommodation of the eye. The variable lens comprises at least two optical elements such that, first, at least one element can move in a direction perpendicular to the optical axis and, second, each of the elements comprises at least one free-form optical surface with such a shape that only the combination of free-form surfaces produces different focusing powers at a different relative positions of the optical elements. For example, the lens construction may consist of the anterior optical element, i.e. the element facing the cornea, which remains fixed and the posterior element which moves in a direction perpendicular to the optical axis. The degree of focusing of the lens, i.e. accommodative response of the eye, is determined by the relative displacement of the optical elements.

The construction also includes, for mechanical functions, at least one haptic for movement, which haptic is coupled to at least one driving means. The haptic for movement is adapted to provide transfer of movement of said driving means to at least one of the optical elements. Experience in clinical trials shows that in a number of human eyes such accommodating lenses with only haptics for movement can be pushed forward by the ciliary muscle which contracts, also in the phakic eye, i.e. eye with a natural lens, in an inward direction but also slightly forward direction, which forward movement can push the construction out of the sulcus into the iris-root. So, at least one haptic for sulcus fixation can be added to said lens construction which haptic is coupled to at least one component of the construction and which haptic is adapted to provide fixation of at least one said component into the sulcus of the eye which fixation is adapted to provide limitation of movement of at least one component of the construction along at least one axis.

Such said accommodating intraocular lenses comprising shifting optical elements are disclosed/referred to, in the following prior art documents, all of which prior art documents are deemed to be included in the present document by said disclosure/reference: optical correction surfaces for such lenses, as in, for example, WO2013055212 and other applications covering same disclosures, and, haptic combinations for such lenses, as in, for example, WO2012105843 and other applications covering same disclosures, and adjustable lenses, as in, for example, US2012323320 and other applications covering same disclosures, and, such lenses driven by ciliary mass, as in, for example, US2012310341 and other applications covering same disclosures, and, intraocular lenses for variable focus, as in, for example, US2012323321 and other applications covering same disclosures, and, optics with simultaneous variable correction of aberrations, as in, for example, US2012257278 and other applications covering same disclosures, and, lenses for variable shift, as in, for example, WO2010131955 and other applications covering same disclosures, and, adjustable lenses and positioning means, as in, for example, US2010280609 and other applications covering same disclosures, and, a largely Ω-shaped haptics for low PCO, as in, for example, US2010106245 and other applications covering same disclosures, and, lenses with variable corrections, as in, for example, US2010094413 and other applications covering same disclosures, and, optical correction surfaces for such lenses, as in, for example, WO2013055212 and other applications covering same disclosures, and specific haptic combinations, as in, for example, WO2012105843, and lenses which can be adjusted, as in, for example, US2012323320 and other applications covering same disclosures, and basic concepts for such lenses, as in, for example, HK1101669 and other applications covering same disclosures, and optical arrangements for such lenses as in, for example, US2008215146 and other applications covering same disclosures, and with such lenses mentioned above driven by the iris of the eye, as in, for example, and, with such lenses with alternative constructions, as in, for example, US2009062912 and CN101137339 and other applications covering same disclosures.

Note that said fixation in the sulcus of the at least one component of the construction, for example a haptic for movement, or, alternatively, an optical element, for example, the anterior optical element, can limit movement of said element in the direction along the Z-axis while allowing free movement, for example, in the X-axis direction to provide variable optical power for accommodation. Alternatively, in the above example, the anterior element can be fixed almost completely with respect to the sulcus of the eye. In this case, variable focusing of the lens construction is reached by movement of the posterior element. Optical designs of accommodating lenses with only one moving element according to optical principles set forth above have been proven to provide ample accommodative response of the eye while maintaining its optical performance close to diffraction-limited performance.

The direction of movement of at least one optical element can coincide with the direction of sulcus fixation, or, alternatively, the direction of sulcus fixation can be perpendicular to the direction of said movement, or, alternatively, the directions can have any other mutual angle. Note that the X-axis and Y-axis comprise the X-Y-plane which plane, in turn, is positioned perpendicular to the Z-axis, for all practical purposes defined as the optical axis of the eye. The X-Y-plane is the plane over which at least one of the optical elements moves. For example, the X-Y-plane coincides with the sulcus plane of the eye. In the present document the X-axis is defined as the axis of movement of optical elements. The haptic for sulcus fixation can be adapted to provide fixation of the lens construction along the Y-axis, perpendicular to the axis for movement, or, alternatively, along the X-axis, parallel to the axis for movement. In the later case, the elasticity of the haptic for sulcus fixation should exceed the elasticity of the haptic for movement ensuring proper mechanical functioning of the lens construction.

The haptics for sulcus fixation can be made such that its elasticity in the X-Y plane greatly exceeds its elasticity in the direction of the Z-axis; hereafter, high elasticity means soft material. Thus, the optical elements of the lens construction are easy to move in the X-Y plane while they remain at fixed Z-axis position. The haptics for sulcus fixation can be manufactured from a different material than the rest of the construction, for example, be manufactured from PMMA while the rest of the construction is manufactured from foldable intraocular lens material. To provide difference in elasticity, the haptics for sulcus fixation can have different thickness, cross section and shape in different directions.

In one of the preferred embodiments, the lens construction may include at least one haptic for sulcus fixation with a largely C-loop type shape as illustrated, for example, in JP2006034917. This haptic for sulcus fixation can be connected to at least one of the haptics for movement having a largely Ω-shape as illustrated, for example, in US2010106245 (this example for a lens with for one element). In other preferred embodiment, at least one of the haptics for sulcus fixation can be connected directly to the anterior optical element. In this case, the haptics for sulcus fixation can also have a largely Ω-shape, or, alternatively, a plate-haptic shape as illustrated, for example, in MX2011005583, or, alternatively, a T-shaped haptic, as can be seen, for example, in JP2005161075.

The mentioned above driving means, causing movement of the optical elements (or at least one element) via the haptics (or at least one haptic) for movement, may include at least one of the natural driving means in the eye, for example, the ciliary muscle of the eye or any tissues and part of the eye producing mechanical pressure/force in the course of accommodation. Alternatively, said driving means are any artificial driving means including, for example, electromechanical, piezoelectric, and various MEMS artificial driving means.

BRIEF DESCRIPTION OF THE DRAWINGS

FIG. 1: Haptics for sulcus fixation attached to an intraocular lens having a lens of fixed optical power 30 and a lens of variable optical power. The lens of variable optical Power includes an anterior optical element, 1, and a posterior optical element 2 each of which include a free-form surface 35. A largely Ω-shaped spring-like haptic for movement is provided to allow movement of the anterior optical element, 3, and a largely Ω-shape spring-like haptic for movement to allow movement of the posterior optical element, 4, with, in this particular embodiment, four haptics for sulcus fixation, of a C-loop type, 5, attached to the largely Ω-shape spring-like haptic of the anterior optical element. The axis for movement, 6, is the axis along which movement, indicated by arrow, 7, drives accommodation by shifting said optical elements in a direction perpendicular to the optical axis. The axis for sulcus fixation, 8, indicates the direction in which the haptics fixated the lens construction in the sulcus, which is, in this particular embodiment, a direction largely perpendicular to the optical axis. Note that in alternative embodiments these four haptics for sulcus fixation can be connected in pairs to form a circular, or an oval, or another shape, sulcus ring.

FIG. 2: An alternative embodiment comprising only two haptics for sulcus fixation. For explanation of lens components and other explanations refer to FIG. 1.

FIG. 3: An alternative embodiment comprising two haptics for sulcus fixation, of a C-loop type, attached to, in this particular embodiment, the anterior optical element. For explanation of lens components and other explanations refer to FIGS. 1, 2.

FIG. 4: An alternative embodiment comprising only two haptics, of a plate haptics type, for sulcus fixation attached to, in this particular embodiment, the anterior optical element. For explanation of lens components and other explanations refer to FIGS. 1, 2.

FIG. 5: The shape of the haptics for sulcus fixation can be a C-loop, 12, or, alternatively, can be of any other shape, for example have a shape with a plateau dedicated to sulcus fixation, 13, as in FIG. 6 (for two alternative top-views related to these figures refer also to FIGS. 11, 12).

FIG. 7: Alternative lens design in which the direction of sulcus fixation coincides with the direction of movement of the optical elements, with a largely oval ring-like haptic, 14, with, in this particular embodiment, two springs, 15, which can be Ω-shaped springs, a stopper-component, 16, which limits the degree of extension of the lens construction (refer to FIG. 13 for an alternative embodiment of such design).

FIG. 8: Alternative lens design in which the direction of sulcus fixation can coincide with the direction of movement of the optical elements, with a largely circular ring-like haptic, 17, with, in this particular embodiment, three stopper-components for each optical element, 18, 19, 20, 21, which stoppers are arrange such that compression of the ring along the axis for movement, 6, results in movement of the optical elements along the axis for movement and fixation in the sulcus in the direction of sulcus fixation, 8. Note that the degree of movement and the degree of fixation can be increased by provision of an oval shaped haptic, 17, with the long dimension of the oval parallel to the axis for sulcus fixation and the shorter dimension of the oval parallel to the axis for movement, so the range of accommodation can be affected by the shape of the oval.

DESCRIPTION OF THE INVENTION

Figure 9:
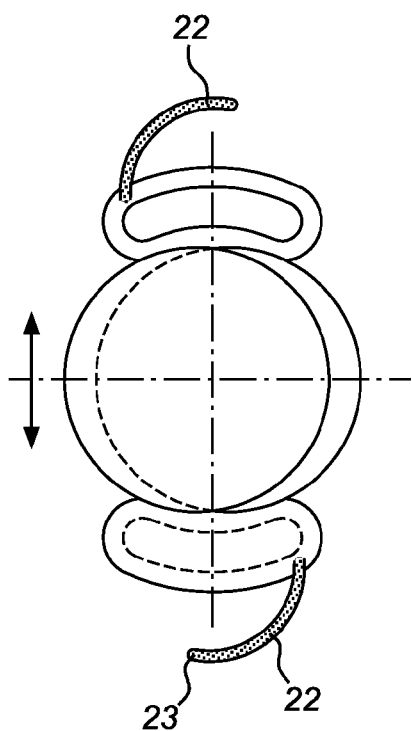
FIG. 9, 10 provide example of embodiments of haptics for sulcus fixation, 22, 24, in combination with lens constructions which are similar to the constructions provided in FIGS. 1-4, with the haptics for sulcus fixation positioned such that the direction of sulcus fixation is coincidental, parallel to, the direction of movement, with the tips of the haptics which can be rigid, to increase firmness of fixation, or, alternatively, flexible, to allow maximum movement of the optical element, or of any intermediate rigidity to provide any combination of said firmness and said movement.
Figure 10:
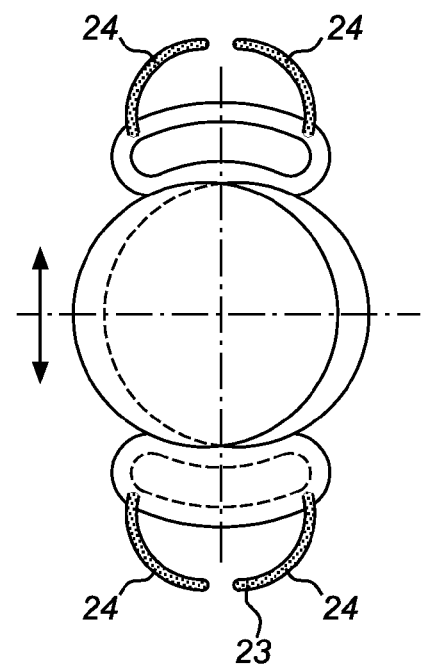
Figure 11:
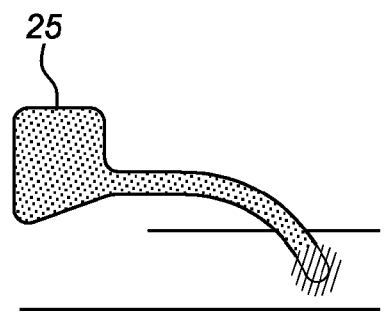
FIG. 11, 12: The shape of alternative embodiments of the haptics for sulcus fixation in the X-Y plane with a paddle shape, 25, and a ragged/toothed shape, 26, both shapes providing increased fixation in the sulcus (examples of shapes of such haptics in the Z-plane are shown in FIGS. 5, 6).
Figure 12:
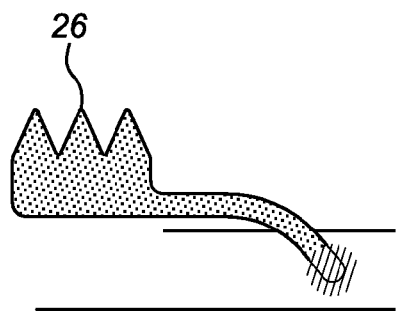

The present document discloses an accommodating intraocular lens construction including, for optical functions:

first, at least one lens of fixed optical power to correct refractive error of the aphakic eye and, second, at least one lens of variable optical power to restore accommodation of the eye. The lens of variable optical power, in turn, may include at least two optical elements of which at least one element can move in a direction perpendicular to the optical axis, moreover, each of the optical elements comprises at least one free-form optical, or aspherical, surface with such a shape that only the combination of free-form surfaces produces different focusing powers at different relative positions of the elements as described in US2012310341 (in part), and, HK1101669, and, US2009062912. Alternatively, the variable lens consists of at least two optical elements of which at least one element can move in a direction along to the optical axis, i.e. in our notations along the Z-axis. In this case, each of the optical elements comprises at least one rotationally symmetrical, e.g. spherical, surface such that the combination of surfaces provides different focusing powers at different positions of at least one optical element relative to the other optical element. Such a variable lens can be a telescope, as set forth in US2012310341 (in part), and, US2012310342 (in full); the variable lens can be a telescope comprising at least one lens of positive optical power on each of the optical elements, or, alternatively, which variable lens can be a telescope comprising at least one lens of positive optical power on one optical element and a lens of negative optical power on the other optical element.

The mechanical arrangement of the accommodating intraocular lens construction includes: first, at least one haptic for movement which is coupled to at least one of the driving means in the eye and adapted to provide transfer of movement of said driving means to at least one of said optical elements and, second, at least one haptic for sulcus fixation providing limitation of movement of at least one component of the lens construction along at least one axis. For example, the haptic for sulcus fixation can be adapted to provide fixation of the lens construction along the Y-axis which is perpendicular to the X-axis, which is the axis of movement of least one of the optical elements. Alternatively, the haptic for sulcus fixation can provide fixation of the lens construction along the X-axis which is also the axis of movement of the optical elements. At least one of the haptics for sulcus fixation can be connected to at least one of the haptics for movement or, alternatively, at least one of the haptics for sulcus fixation can be connected directly to one of the optical elements, for example, the anterior element. Alternatively, the lens construction can comprise a combination of at least two haptics for sulcus fixation which combination includes at least one haptic for sulcus fixation connected to any component of the construction and at least one haptic for sulcus fixation connected to any other component of the construction. Alternatively, the lens construction can comprise a combination of at least one haptic for sulcus fixation which is connected to one of the haptics for movement and at least one haptic for sulcus fixation which is connected to an optical element, with at least one haptic for sulcus fixation which has a, largely, Ω-shape, or, alternatively, with at least one haptic for sulcus fixation which has a, largely, C-loop type shape, or, alternatively, with at least one haptic for sulcus fixation which has a, largely, plate-haptic shape, or, alternatively, with at least one haptic for sulcus fixation which has a, largely, T-shape, with the construction comprising at least one haptic for movement adapted to provide transfer of movement from at least one natural driving means in the eye to at least one of the optical elements, which at least one haptic for movement can be adapted to provide transfer of movement from the ciliary muscle of the eye to at least one of the optical elements, or, alternatively, with the construction comprising at least one haptic for movement adapted to provide transfer of movement from at least one artificial driving means in the eye to at least one of the optical elements, which can be at least one MEMS driving means in the eye to at least one of the optical elements, with the construction comprising at least one haptic for sulcus fixation which is flexible in the X-Y plane, the plane perpendicular to the optical axis, which flexibility exceeds by at least a factor 10 the flexibility in the direction of the Z-plane, the plane parallel to the optical axis, with the construction which can comprise at least one haptic for sulcus fixation which is manufactured from at least one different material than the at least one material from which the rest of the construction is manufactured, which material for the haptic for sulcus fixation can be poly-methyl-methacrylate, PMMA, with the construction adapted to provide, to the aphakic human eye, a combination of correction of fixed refractive error and restoration of accommodation.

Furthermore, the haptics for sulcus fixation can also be a ring which can be a permanent component of the construction or which can be a separate element to be fixed to the construction in the eye or alternatively be coupled to but remain separated from the construction in the eye. So, the combination of an accommodating intraocular lens and at least one intraocular positioning component is such that the positioning component is adapted to fit in the sulcus of the eye and that the positioning component is fitted with at least one connection component which is adapted to provide connection to at least one component of the lens. In the preferred embodiment the positioning component is a sulcus ring which ring can be a fully closed ring or, alternatively, a ring with at least one opening along the circumference.

The positioning component can comprise at least one form fitting component which is adapted to provide a connection with the lens which form fitting component is at least one ridge adapted to provide said connection with the lens which comprises at least one groove adapted to fit with said ridge, or, alternatively, the form fitting component is at least one groove adapted to provide said connection with the lens which comprises at least one ridge adapted to fit with said groove.

The invention claimed is:

1. An accommodating intraocular lens (AIOL) having an optical axis comprising:
    a lens of variable optical power including an anterior optical element and a posterior optical element of which at least one is movable relative to the other in a direction perpendicular to the optical axis, each of the anterior optical element and the posterior optical element having at least one free-form optical surface such that they exhibit, in combination, different focusing power at different relative positions of one optical element relative to the other optical element in a plane perpendicular to the optical axis;
    at least one lens of fixed optical power associated with the lens of variable optical power for correcting refractive error;
    at least two spring like haptics for movement, one of said at least two spring like haptics for movement attached to the anterior optical element, the other of said at least two spring like haptics for movement attached to the posterior optical element, each of said at least two haptics for movement extending in a plane substantially perpendicular to the optical axis and comprising ciliary muscle-engaging surfaces, the at least two spring like haptics for movement are adapted and dimensioned to be directly coupled to the ciliary muscle of the eye to provide transfer of movement of the ciliary muscle to at least one of said anterior and posterior optical elements to mutually shift the anterior and posterior optical elements in opposite directions relative to each other along said direction perpendicular to the optical axis, wherein the degree of movement of the optical elements depends on the degree of force exerted onto the at least two spring like haptics for movement by the ciliary muscle; and a first pair of haptics for sulcus fixation attached to the haptic for movement attached to the anterior optical element, the first pair of haptics for sulcus fixation extending in a plane substantially perpendicular to the optical axis and comprising sulcus-engaging surfaces, the first pair of haptics for sulcus fixation adapted and dimensioned to be directly coupled to the sulcus of the eye to limit movement of the anterior optical element along the optical axis, the first pair of haptics for sulcus fixation having a C-loop shape and a greater elasticity than the haptic for movement attached to the anterior optical element, a second pair of haptics for sulcus fixation attached to the haptic for movement attached to the posterior optical element, the second pair of haptics for sulcus fixation extending in a plane substantially perpendicular to the optical axis and comprising sulcus-engaging surfaces, the second pair of haptics for sulcus fixation adapted and dimensioned to be directly coupled to the sulcus of the eye to limit movement of the posterior optical element along the optical axis, the second pair of haptics for sulcus fixation having a C-loop shape and a greater elasticity than the haptic for movement attached to the posterior optical element, and wherein the at least two spring like haptics for movement have a different shape than the first and second pairs of haptics for sulcus fixation, wherein each of the at least two spring like haptics for movement comprises an $\Omega$-shape.

2. The AIOL according to claim 1, wherein the first and second pairs of haptics for sulcus fixation are flexible in the X-Y plane, the plane perpendicular to the optical axis, which flexibility exceeds by at least a factor 10 the flexibility in the direction of the Z-plane, the plane parallel to the optical axis.

3. The AIOL according to claim 1, wherein the first and second pairs of haptics for sulcus fixation are manufactured from at least one different material than at least one material from which the rest of the AIOL is manufactured.

4. The AIOL according to claim 3, wherein the AIOL comprises at least one haptic for sulcus fixation which is manufactured from poly-methyl-methacrylate.

* * * * *